US006248137B1

(12) United States Patent
Terranova et al.

(10) Patent No.: US 6,248,137 B1
(45) Date of Patent: Jun. 19, 2001

(54) COMPOSITIONS FOR DYEING KERATINOUS FIBRES, CONTAINING 3-AMINOPYRAZOLO [1,5-A]PYRIMIDINES, METHOD OF DYEING AND NOVEL 3-AMINOPYRAZOLO [1,5-A]PYRIMIDINES

(75) Inventors: Eric Terranova, Bois Colombes; Aziz Fadli, Chelles; Alain Lagrange, Coupvray, all of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/204,559

(22) Filed: Dec. 3, 1998

(30) Foreign Application Priority Data

Dec. 3, 1997 (FR) .................................................. 97 15244

(51) Int. Cl.$^7$ ....................................................... A61K 7/13
(52) U.S. Cl. ................................ 8/409; 423/567; 423/573
(58) Field of Search ................................ 8/407, 406, 409, 8/423, 573, 567; 544/281; 548/360.5

(56) References Cited

U.S. PATENT DOCUMENTS

| 3,925,385 | 12/1975 | O'Brien et al. ...................... 544/281 |
| 5,234,818 | 8/1993 | Zimmermann et al. ............... 435/28 |
| 5,334,505 | 8/1994 | Zimmermann et al. ............... 435/18 |
| 5,380,340 | 1/1995 | Neunhoeffer et al. .................... 8/409 |
| 5,457,200 | 10/1995 | Zimmermann et al. ............. 544/281 |

FOREIGN PATENT DOCUMENTS

| 2 257 547 | 6/1973 | (DE) . |
| 2 920 537 | 11/1979 | (DE) . |
| 4 029 324 | 3/1992 | (DE) . |
| 4 133 957 | 4/1993 | (DE) . |
| 0 433 854 | 6/1991 | (EP) . |
| 0 433 855 | 6/1991 | (EP) . |
| 0 628 559 | 12/1994 | (EP) . |
| 2 586 913 | 3/1987 | (FR) . |
| WO 97/49378 | 12/1997 | (WO) . |

OTHER PUBLICATIONS

G. Muhmel et al., "Pyrazolo [1,5–a]purimidine aus 3–Alkoxyacroleinen und 5–Amino–1H–pyrazolen", International Journal of Methods in Snythetic Organic Chemistry, No. 8, Aug. 1982, pp. 673–677.

J. Backes et al., Organische Stickstoff–Verbindungen IV, 1992, pp. 815.

Siya Ram et al., "Ammonium Format in Organic Synthesis: A Versatile Agent in Catalytic Hydrogen Transfer Reductions", Journal of Synthetic Organic Chemistry, No. 2, Feb. 1988, pp. 91–95.

Robert H. Springer, "Synthesis and Enzymic Activity of 6–Carbethoxy–and 6–Ethoxy–3,7–disubstituted–pyrazolo [1,5–a]pyrimidines and Related Derivatives as Adenosine Cyclic 3',5'–Phosphate Phosphodiesterase Inhibitors", Journal of Medical Chemistry, vol. 25, No. 3, Mar. 1982, pp. 235–242.

William E. Kirkpatrick et al., "3–Halo–5,7–dimethylpyrazolo[1,5–a]pyrimidines, a Nonbenzodiazepinoid class of Antianxiety Agent Devoid of Potentiation of Central Nervous System Depressant Effects of Ethanol or Barbiturates", Journal of Medicinal Chemistry, vol. 20, No. 3, Mar. 1977, pp. 386–393.

Katsuhiko Nagahara et al., "Reaction of 5–Aminopyrazole Derivatives with Ethoxymethylene–malononitrile and its Analogues", Journal of Heterocyclic Chemistry, vol. 31, No. 1, Jan.–Feb. 1994, pp. 239–243.

Keitaro Senga et al., "Synthesis and Antitrichomonal Activity of Certain Pyrazolo[1,5–a]pyrimidines", Jounral of Medical Chemistry, vol. 18, No. 3, Mar. 1975, pp. 312–314.

Helmut Dorn et al., "Über die elektrophile Substitution von3(5)–Amino–pyrazol", Liebigs Ann. Chem. 707, 1967, pp. 141–146.

English Language Derwent Abstract of DE 2 920 537, Nov. 1979.

English Language Derwent Abstract of DE 4 029 324, Mar. 1992.

English Language Derwent Abstract of FR 2 586 913, Mar. 1987.

T.H. James, The Theory of the Photographic Process, 3rd Edition, the Macmillan Co, NY, Chapter 17, pp. 382–396, 1966.*

Venkataraman, The Chemistry of Synthetic Dyes, vol. V, Academic Press, NY & London, p. 483, 1966.*

* cited by examiner

Primary Examiner—Caroline D. Liott
(74) Attorney, Agent, or Firm—Finnegan, Henderson, Farabow, Garrett & Dunner L.L.P.

(57) ABSTRACT

The invention relates to novel compositions for the oxidation dyeing of keratinous fibers, comprising at least one 3-aminopyrazolo[1,5-a]-pyrimidine, to the method of dyeing which employs this composition, to novel 3-aminopyrazolo[1,5-a]pyrimidines and to the process for their preparation.

56 Claims, No Drawings

COMPOSITIONS FOR DYEING KERATINOUS FIBRES, CONTAINING 3-AMINOPYRAZOLO [1,5-A]PYRIMIDINES, METHOD OF DYEING AND NOVEL 3-AMINOPYRAZOLO [1,5-A]PYRIMIDINES

The invention relates to novel compositions for the oxidation dyeing of keratinous fibers, comprising at least one 3-aminopyrazolo[1,5-a]-pyrimidine as an oxidation base, the method of dyeing which employs this composition, novel 3-amino-pyrazolo[1,5-a]pyrimidines, and the process for their preparation.

It is well known to dye keratinous fibers, and in particular human hair, using dyeing compositions comprising oxidation dye precursors, such as ortho- or para-phenylenediamines and ortho- or para-aminophenols, and heterocyclic compounds, such as diaminopyrazole derivatives, which are generally referred to as oxidation bases. The oxidation dye precursors, or oxidation bases, are colorless or lightly colored compounds which, when combined with oxidizing products, are able to give rise to colored compounds and dyes by a process of oxidative condensation. These compounds have the common feature of possessing one amino group and one hydroxyl group or two amino groups, which give them their oxidation-base character.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The diversity of molecules employed as oxidation bases and couplers makes it possible to obtain a wide range of colors.

The "permanent" coloration obtained by these oxidation dyes should optimally meet, certain conditions. Hence it should have no toxicological effects, should allow shades of the desired intensity to be obtained, and should have good resistance to external agents (light, inclement weather, washing, permanent-waving, perspiration and friction).

The dyes should also allow white hairs to be covered and, finally, they should be as unselective as possible - in other words, they should allow the smallest possible differences in coloration to be produced over the entire length of a single keratinous fiber, which may vary in condition of sensitization or damage from its tip to its root.

Patent application DE 4 029 324 proposes the use of certain 2-hydroxypyrazolo[1,5-a]pyrimidines, which may be substituted by $C_1$–$C_4$ alkyl radicals in positions 4, 5 and/or 6, as couplers for the oxidation dyeing of keratinous fibers.

Patent application DE 4 133 957 also proposes the use of certain pyrazolo-[1,5-a]pyrimidine derivatives, belonging to the class of the tetrahydropyrazolo[1,5-a]pyrimidines, as oxidation dye precursors for the oxidation dyeing of keratinous fibers.

The inventors have now made the unexpected and surprising discovery that a new class of 3-aminopyrazolo[1,5-a]pyrimidines of formula (I) defined below, some of which are themselves novel, are suitable for use as an oxidation base. These compounds contain only a single amino group that makes it possible to obtain dyeing compositions which lead to colorations which are strong and have good resistance to external agents (light, inclement weather, washing, permanent-waving, perspiration and friction). Finally, these compounds can be easy to synthesize.

These discoveries form the basis of the present invention.

The invention therefore provides a composition for the oxidation dyeing of keratinous fibers, and in particular human keratinous fibers such as hair, that comprises, in a medium suitable for dyeing, at least one 3-aminopyrazolo [1,5-a]pyrimidine chosen from compounds of formula (I) below and acid and base addition salts thereof, as oxidation base:

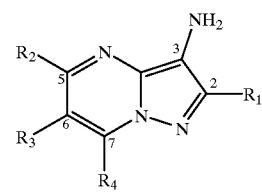

(I)

in which
$R_1$, $R_2$, $R_3$ and $R_4$ are identical or different and represent a hydrogen atom, a halogen atom, a $C_1$–$C_4$ alkyl radical, a $C_1$–$C_4$ trifluoroalkyl radical, a $C_1$–$C_4$ alkoxy radical, an aryl radical, a $C_1$–$C_4$ monohydroxyalkyl radical, a $C_2$–$C_4$ polyhydroxyalkyl radical, a $C_1$–$C_4$ ($C_1$–$C_4$ alkoxy)alkyl radical, a $C_1$–$C_4$ aminoalkyl radical, a $C_1$–$C_4$ ($C_1$–$C_4$ alkyl)aminoalkyl radical, a $C_1$–$C_4$ di($C_1$–$C_4$ alkyl)aminoalkyl radical, a $C_1$–$C_4$ monohydroxy ($C_1$–$C_4$ alkyl)aminoalkyl radical or a $C_1$–$C_4$ di[hydroxy($C_1$–$C_4$ alkyl)]aminoalkyl radical.

Among the 3-aminopyrazolo[1,5-a]pyrimidines of formula (I) which can be used as an oxidation base in the compositions in accordance with the invention generally preferred 3-aminopyrazolo[1,5-a]pyrimidines are:

pyrazolo[1,5-a]pyrimidin-3-ylamine;
5,7-dimethylpyrazolo[1,5-a]pyrimidin-3-ylamine;
5,6,7-trimethylpyrazolo[1,5-a]pyrimidin-3-ylamine;
7-methylpyrazolo[1,5-a]pyrimidin-3-ylamine;
5,6,7-trimethylpyrazolo[1,5-a]pyrimidin-3-ylamine;
7-methylpyrazolo[1,5-a]pyrimidin-3-ylamine;
5-methylpyrazolo[1,5-a]pyrimidin-3-ylamine;
7-methoxy-5-methylpyrazolo[1,5-a]pyrimidin-3-ylamine;
2,5,6,7-tetramethylpyrazolo[1,5-a]pyrimidin-3-ylamine;
2-methoxy-5,7-dimethylpyrazolo[1,5-a]pyrimidin-3-ylamine;
5,7-di-tert-butylpyrazolo[1,5-a]pyrimidin-3-ylamine;
5,7-di-trifluoromethylpyrazolo[1,5-a]pyrimidin-3-ylamine;
2,6-dimethylpyrazolo[1,5-a]pyrimidin-3-ylamine;
2-chloro-5,7-dimethylpyrazolo[1,5-a]pyrimidin-3-ylamine;
7-methyl-2-tert-butyl-5-trifluoromethylpyrazolo-[1,5-a]pyrimidin-3-ylamine; and the acid or base addition salts thereof.

Among the 3-aminopyrazolo[1,5-a]pyrimidines of formula (I) which can be used as an oxidation base in the compositions in accordance with the invention particularly preferred 3-aminopyrazolo [1,5-a]pyrimidines are:

pyrazolo[1,5-a]pyrimidin-3-ylamine;
5,7-dimethylpyrazolo[1,5-a]pyrimidin-3-ylamine;
5,6,7-trimethylpyrazolo[1,5-a]pyrimidin-3-ylamine;
2,5,6,7-tetramethylpyrazolo[1,5-a]pyrimidin-3-ylamine;
2-methoxy 5,7-dimethylpyrazolo[1,5-a]pyrimidin-3-ylamine;

5,7-di-trifluoromethylpyrazolo[1,5-a]pyrimidin-3-ylamine;

7-methylpyrazolo[1,5-a]pyrimidin-3-ylamine;

5-methylpyrazolo[1,5-a]pyrimidin-3-ylamine; and the acid or base addition salts thereof.

The great majority of the 3-aminopyrazolo[1,5-a] pyrimidines of formula (I) are compounds which are known in the pharmaceutical field and are described, in particular, in patent applications EP-A-0 433 854 and EP-A-0 433 855.

The 3-aminopyrazolo[1,5-a]pyrimidine or -pyrimidines of formula (I) above makes or make up preferably from 0.0005 to 12% by weight approximately relative to the total weight of the dyeing composition and, more preferably, from 0.005 to 6% by weight, approximately, of the total weight.

A medium (or vehicle) suitable for dyeing is, for example, water, water/alcohol mixtures, and a mixture of water and at least one organic solvent to dissolve any compounds which are not sufficiently water soluble. Preferred organic solvents are, for example, $C_1$–$C_4$ lower alkanols, such as ethanol and isopropanol; glycerol; glycols and glycol ethers such as 2-butoxyethanol, propylene glycol, propylene glycol monomethyl ether and diethylene glycol monoethyl and monomethyl ether, and aromatic alcohols such as benzyl alcohol or phenoxyethanol, similar products and mixtures thereof.

The solvents can be present in proportions preferably ranging from 1 to 40% by weight approximately relative to the total weight of the dyeing composition, and even more preferably from 5 to 30% by weight approximately.

The pH of the dyeing composition in accordance with the invention generally ranges from 3 to 12, approximately, and preferably approximately from 5 to 11. It can be adjusted to the desired value by means of acidifying or basifying agents commonly used in the dyeing of keratinous fibers, or by using conventional buffer systems.

Preferred acidifying agents include, for example, mineral acids or organic acids, such as hydrochloric acid, orthophosphoric acid, sulphuric acid, carboxylic acids such as acetic acid, tartaric acid, citric acid and lactic acid, and sulphonic acids.

Preferred basifying agents include, for example, of aqueous ammonia, alkali metal carbonates, alkanolamines such as mono-, di- and triethanolamines and derivatives thereof, sodium hydroxide, potassium hydroxide, and the compounds of the following formula (II):

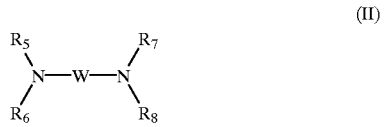

(II)

in which W is a propylene residue optionally substituted by a hydroxyl radical or a $C_1$–$C_4$ alkyl radical; $R_5$, $R_6$, $R_7$ and $R_8$, which may be identical or different, represent a hydrogen atom, a $C_1$–$C_4$ alkyl radical or a $C_1$–$C_4$ hydroxyalkyl radical.

In a preferred embodiment, the oxidation dyeing composition in accordance with the invention additionally includes at least one coupler in order to modify or enrich with glints the shades obtained by employing the compounds of formula (I).

The couplers which can be used in the oxidation dyeing compositions in accordance with the invention may be chosen from the couplers used conventionally in oxidation dyeing, among which generally preferred couplers are: meta-phenylenediamines, meta-aminophenols, meta-diphenols and heterocyclic couplers.

More particularly preferred couplers are chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethoxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and the addition salts thereof.

When present, the coupler(s) preferably represent(s) from 0.0001 to 10% by weight approximately relative to the total weight of the dyeing composition, and even more preferably from 0.005 to 5% by weight approximately relative to this weight.

The dyeing composition in accordance with the invention may additionally comprise, as well as the above-defined dyes, at least one additional oxidation base chosen from the oxidation bases which are conventionally employed in oxidation dyeing, among which preferred oxidation bases are: para-phenylenediamines, bisphenylalkylenediamines, para-aminophenols, ortho-aminophenols and heterocyclic bases which are different from the 3-aminopyrazolo[1,5-a]-pyrimidines of formula (I) that are employed in accordance with the invention.

Among the para-phenylenediamines, preferred para-phenylenediamines are: para-phenylenediamine, para-tolylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and the acid addition salts thereof.

Among the abovementioned para-phenylenediamines more preferred para-phenylenediamines are: para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl- para-phenylenediamine, 2,3-dimethyl-para-phenylenediamine, N,N'-bis(β-hydroxyethyl)-para-phenylenediamine, 2-chloro-para-phenylenediamine, 2-β-acetylaminoethyloxy-para-phenylenediamine, and the acid addition salts thereof.

Among the bisphenylalkylenediamines preferred bisphenylalkylenediamines are: N,N'-bis(β-hydroxyethyl)-N,N'-bis(4'-aminophenyl)-1,3-diaminopropanol, N,N'-bis(β- hydroxyethyl)-N,N'-bis(4'-aminophenyl)ethylenediamine, N,N'-bis(4-aminophenyl)-tetramethylenediamine, N,N'-bis (β-hydroxyethyl)-N,N'-bis(4-aminophenyl) tetramethylenediamine, N,N'-bis(4methylaminophenyl) tetramethylenediamine, N,N'-bis(ethyl)-N,N'-bis(4'-amino-3'-methylphenyl)-ethylenediamine, 1,8-bis(2,5-diaminophenoxy)-3,5-dioxaoctane, and the acid addition salts thereof.

Among the para-aminophenols, preferred para-aminophenols are: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Among the ortho-aminophenols, preferred ortho-aminophenols are: 2-aminophenol, 2-amino-5-methylphenol, 2-amino-6-methylphenol, 5-acetamido-2-aminophenol, and the acid addition salts thereof.

Among the heterocyclic bases, preferred heterocyclic bases are: pyridine derivatives, pyrimidine derivatives and pyrazole derivatives.

When used, the additional oxidation base(s) preferably represent(s) from 0.0005 to 12% by weight approximately relative to the total weight of the dyeing composition and, more preferably from 0.005 to 6% by weight approximately relative to this weight.

In general terms, the acid addition salts used within the scope of the dyeing compositions of the invention (compounds of formula (I), additional oxidation bases and couplers) are chosen in particular from hydrochlorides, hydrobromides, sulphates, citrates, succinates, tartrates, lactates and acetates.

The base addition salts used within the scope of the dyeing compositions of the invention (compounds of formula (I), additional oxidation bases and couplers) are chosen from sodium hydroxide solution, potassium hydroxide solution, aqueous ammonia, or amines.

The dyeing composition in accordance with the invention can additionally comprise one or more direct dyes which can be chosen in particular from the nitrated dyes of the benzene series.

The dyeing composition in accordance with the invention can also contain various adjuvants used conventionally in hair dyeing compositions, such as anionic, cationic, nonionic, amphoteric or zwitterionic surfactants or mixtures thereof, anionic, cationic, nonionic, amphoteric or zwitterionic polymers or mixtures thereof, organic or inorganic thickeners, antioxidants, penetration agents, sequestrants, fragrances, buffers, dispersants, conditioners such as, for example, modified or unmodified, volatile or nonvolatile silicones, film formers, ceramides, preservatives and opacifiers.

The person skilled in the art can select the optional complementary compound(s) such that the advantageous properties intrinsically associated with the dyeing composition in accordance with the invention are not, or not substantially, adversely affected by the additions envisaged.

The dyeing composition according to the invention may be in various forms, such as in the form of liquids, creams, gels or any other form which is suitable for dyeing keratinous fibers, and in particular human hair.

The invention also provides a process for dyeing keratinous fibers, and in particular human keratinous fibers such as hair using the dyeing composition as defined above.

According to this process, at least one dyeing composition as defined above is applied to the fibers for a period which is sufficient to develop the desired coloration either in air or with the aid of an oxidizing agent. The dyeing composition can optionally include oxidation catalysts in order to accelerate the process of oxidation.

According to one embodiment of the process of the invention, the dyeing of the fibers can be carried out without the addition of an oxidizing agent, solely by contact with the oxygen in the air.

According to another embodiment of the process of the invention at least one dyeing composition as defined above is applied to the fibers, the color being developed at an acidic, neutral or alkaline pH with the aid of an oxidizing agent which is added right at the time when the dyeing composition is employed or which is present in an oxidizing composition which is applied simultaneously or sequentially and separately.

According to this embodiment of the dyeing process of the invention, the above-described dyeing composition is preferably mixed at the time of use with an oxidizing composition comprising, in a medium suitable for dyeing, at least one oxidizing agent which is present in an amount sufficient for color development. The resulting mixture is subsequently applied to the keratinous fibers and left to act for approximately 3 to 50 minutes, preferably for approximately 5 to 30 minutes, after which the fibers are rinsed, optionally washed with shampoo, rinsed again and dried.

The oxidizing agent present in the oxidizing composition as defined above can be chosen from the oxidizing agents conventionally used for the oxidation dyeing of keratinous fibers, among which preferred oxidizing agents are: hydrogen peroxide, urea peroxide, alkali metal bromates, and persalts, such as perborates and persulphates, and enzymes, such as peroxidases and oxidoreductases with 2 unpaired electrons. It is particularly preferred to use hydrogen peroxide.

The pH of the oxidizing composition comprising the oxidizing agent as defined above is such that, after it has been mixed with the dyeing composition, the pH of the resulting composition applied to the keratinous fibers preferably ranges from approximately 3 to 12, and more preferably, from 5 to 11. The pH can be adjusted to the desired value by means of acidifying or basifying agents which are commonly employed in the dyeing of keratinous fibers and are as defined above.

The oxidizing composition as defined above can also contain various adjuvants which are conventionally employed in hair-dyeing compositions and are as defined above.

The composition which is ultimately applied to the keratinous fibers can be in various forms, such as in the form of liquids, creams or gels or in any other form suitable for dyeing keratinous fibers, and in particular human hair.

Another aspect of the invention is a multi-compartment dyeing device or "kit" or any other multi-compartment packaging system a first compartment of which contains the dyeing composition as defined above and a second compartment of which contains the oxidizing composition as defined above. These devices may be equipped with a means for delivering the desired mixture onto the hair, such as the devices described in patent FR-2 586 913 the disclosure of which is specifically incorporated by reference herein.

Certain compounds of formula (I) which are used as an oxidation base within the scope of the present invention are novel and, to that extent, are further provided by the invention.

These novel 3-aminopyrazolo[1,5-a]pyrimidines are:
pyrazolo[1,5-a]pyrimidin-3-ylamine;

5,6,7-trimethylpyrazolo[1,5-a]pyrimidin-3-ylamine;
7-methylpyrazolo[1,5-a]pyrimidin-3-ylamine;
5-methylpyrazolo[1,5-a]pyrimidin-3-ylamine;
7-methylpyrazolo[1,5-a]pyrimidin-3-ylamine;
5-methoxypyrazolo[1,5-a]pyrimidin-3-ylamine;
7-methoxy-5-methylpyrazolo[1,5-a]pyrimidin-3-ylamine;
2,5,6,7-tetramethylpyrazolo[1,5-a]pyrimidin-3-ylamine;
5,7-di-tert-butylpyrazolo[1,5-a]pyrimidin-3-ylamine;
5,7-ditrifluoromethylpyrazolo[1,5-a]pyrimidin-3-ylamine; and the acid or base addition salts thereof.

These novel 3-aminopyrazolo[1,5-a]pyrimidines can be prepared by methods which are known and are described in the literature.

For example, a cyclocondensation reaction is carried out between a 3(5)-amino-4-nitropyrazole derivative and a β-keto ester, a β-diketone or a β-keto aldehyde in order to form the pyrazolo[1,5-a]pyrimidine structure. This reaction is carried out in a manner according to the methods described in the following references:

EP-A-628559 BEIERSDORF-LILLY

G. Mühmel, R. Hanke, E. Breitmaier, Synthesis, 673, 1982.

The resulting nitro derivative is subsequently reduced to give the expected 3-amino-pyrazolo[1,5-a]pyrimidine in accordance with known processes (R. Hemmer, W. Lurken in Houben-Weyl, "Methoden der Organischen Chemie" [Methods of Organic Chemistry], Vol. E 16d, p. 815 ff.). Preference is given to the use of metals such as palladium (Pd), platinum (Pt) or nickel (Ni) in the presence of a hydrogen donor such as ammonium formate, formic acid or else cyclohexene in place of hydrogen (S. Ram, R. E. Ehrenkaufer, Synthesis, 91, 1988). It is also possible to use metals such as zinc (Zn), tin (Sn) or iron (Fe) in an acidic medium such as aqueous hydrochloric acid or aqueous acetic acid, optionally with addition of an organic solvent such as methanol, ethanol or tetrahydrofuran.

Alternatively, it is possible to carry out a cyclocondensation reaction between a 3(5)-aminopyrazole derivative and a β-keto ester, a β-diketone or a β-keto aldehyde in order to form the pyrazolo[1,5-a]pyrimidine structure. This reaction is carried out in a manner according to the methods described in the following references:

R. H. Springer, M. B. Scholten, D. E. O'Brien, T. Novinson, J. P. Miller, R. K. Robins, J. Med. Chem., 25,235,1982.

T. Novinson, R. K. Robins, T. R. Matthews, J. Med. Chem., 20, 386,1977.

K. Nagahara, H. Kawano, S. Sasaoka, C. Ukawa, T. Hirama, A. Takada, J. Heterocyclic Chemistry, 239,1994.

It is also possible to carry out a nitration reaction of this pyrazolo[1,5-a]pyrimidine structure by well-known methods. By way of example, reference is made to the following document:

K. Senga, T. Novinson, R. H. Springer, R. P. Rao, D. E. O'Brien, R. K. Robins, H. R. Wilson, J. Med. Chem., 18(3), 312, 1975.

The nitro derivative is subsequently reduced as above to give the expected 3 -aminopyrazolo-[1,5-a]pyrimidine.

The 3-aminopyrazolo[1,5-a]pyrimidines of formula (I) and the addition salts thereof, as defined above, can likewise be used as an oxidation base in and for the preparation of compositions intended for photography or chemical imaging.

The following examples serve to illustrate the invention without, however, limiting its scope.

SYNTHESIS EXAMPLES

EXAMPLE 1

Synthesis of pyrazolo[1,5-a]pyrimidin-3-ylamine hydrochloride

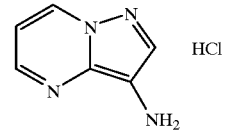

a) Preparation of 3-nitropyrazolo[1,5-a]pyrimidine 44 g of malonaldehyde bisdiethyl acetal, 300 cc of acetic acid and 30 g of 4-nitro-2H-pyrazol-3-ylamine hydrochloride (prepared according to H. Dorn and H. Dilcher, Liebigs Ann. Chem., 707, 141, 1967) were introduced into a 500 ml three-necked round-bottomed flask fitted with a magnetic stirrer, a condenser and a thermometer. The medium was refluxed for 5 hours and then approximately 100 cc of acetic acid were evaporated off. The solid was filtered off and washed with diisopropyl ether. Drying under vacuum and over phosphoric anhydride at 40° C. yielded 27.7 g of 3-nitropyrazolo[1,5-a]pyrimidine (yield=92.5%).

$^1$H NMR (DMSO-$d_6$; 200 MHz): 3.34 (s; 1H); 7.51 (dxd; J1=4.3 Hz and J2=6.9 Hz; 1 H); 9.04 (dxd; J1=4.3 Hz and J3=1.2 Hz; 1 H); 9.09 (s; 1H); 9.44 (dxd; J2=6.9 Hz and J3=1.2 Hz; 1H)

b) Preparation of pyrazolo[1,5-a]pyrimidin-3-ylamine hydrochloride 100 cc of ethanol, 12 cc of water, 3.3 g of ammonium chloride and 10 g of 3-nitropyrazolo[1,5-a]-pyrimidine obtained above in the preceding step were introduced into a 250 ml three-necked round-bottomed flask fitted with a magnetic stirrer, a condenser and a thermometer. The medium was then refluxed. The heating was withdrawn, and 16 g of zinc powder were added in small portions in order to maintain the reflux. When this addition was complete, the mixture was heated at reflux for 3 hours. The zinc salts were filtered off hot. The filtrate was cooled until crystallization took place. The crystalline product was filtered off and dissolved in 100 cc of absolute ethanol. After bubbling gaseous hydrochloric acid through the ethanolic solution, the hydrochloride was precipitated by addition of 1 litre of diisopropyl ether. Drying under vacuum and over phosphoric anhydride yielded 6 g of pyrazolo[1,5-a]-pyrimidin-3-ylamine hydrochloride (red solid) (yield=57.5%).

$^1$H NMR ($D_2O$; 200 MHz): 7.18 (dxd; $J_1$=4.2 Hz and $J_2$=7.1 Hz; 1H); 8.33 (s; 1H); 8.65 (dxd; $J_1$=4.2 Hz and $J_3$=1.6 Hz; 1H); 8.90 (dxd; $J_2$=7.1 Hz and $J_3$=1.6 Hz; 1H)

EXAMPLE 2

Synthesis of 5,6,7-trimethylpyrazolo[1,5-a]pyrimidin-3-ylamine hydrochloride

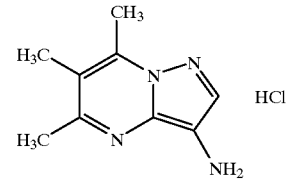

a) Preparation of 5,6,7-trimethyl-3-nitropyrazolo-[1,5-a]pyrimidine 80 cc of acetic acid, 8.2 g of 4-nitro-2H-pyrazol-3-ylamine hydrochloride (prepared according to H. Dorn and H. Dilcher, Liebigs Ann. Chem., 707, 141, 1967) and 7.2 g of 3-methylpentane-2,4-dione were introduced into a 100 ml three-necked round-bottomed flask fitted with a magnetic stirrer, a condenser and a thermometer. The medium was refluxed for 3 hours. The medium was filtered at room temperature and the solid was washed with diisopropyl ether. This yielded 9.4 g of crude product. 3.5 g of this product was recrystallized in 23 cc of absolute ethanol. Drying under vacuum and over phosphoric anhydride yielded 3.1 g of 5,6,7-trimethyl-3-nitropyrazolo[1,5-a]pyrimidine (yield=80%).

hu 1H NMR (DMSO-d$_6$; 200 MHz): 2.31 (s; 3H); 2.62 (s; 3H); 2.75 (s; 3H); 8.89 (s; 1H)

b) Preparation of 5,6,7-trimethylpyrazolo[1,5-a]-pyrimidin-3-ylamine hydrochloride 90 cc of ethanol, 10 cc of water, 1.5 g of ammonium chloride and 6.18 g of 5,6,7-trimethyl-3-nitropyrazolo[1,5-a]pyrimidine obtained above in the preceding step were introduced into a 250 ml three-necked round-bottomed flask fitted with a magnetic stirrer, a condenser and a thermometer. The medium was then refluxed. The heating was withdrawn, and 7.8 g of zinc powder were added in small portions in order to maintain the reflux. When this addition was complete, the mixture was heated at reflux for 1 hour. The zinciferous sludges were filtered off hot. The filtrate was concentrated to a tenth of its volume, and the product which crystallized was filtered off. This product was washed with petroleum ether. Drying under vacuum and over phosphoric anhydride yielded 4.9 g of 5,6,7-trimethylpyrazolo[1,5-a]pyrimidine hydrochloride (yield=82%).

$^1$H NMR (DMSO-d$_6$; 200 MHz): 2.27 (s; 3H); 2.55 (s; 3H); 2.70 (s; 3H); 8.22 (s; 1H); 10.61 (broad s; 3H)

EXAMPLE 3

Synthesis of 7-methylpyrazolo[1,5-a]-pyrimidin-3-ylamine hydrochloride

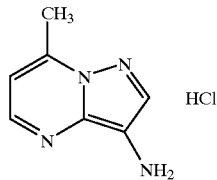

a) Preparation of 7-methyl-3-nitropyrazolo[1,5-a]-pyrimidine

This compound was obtained by following the protocol described in the first step of Example 2. All quantities were multiplied by four and the 3-methylpentane-2,4-dione was replaced by 1.1 molar equivalent of acetylacetaldehyde dimethyl acetal. At the end of the reaction, the green solution was concentrated and poured onto ice. The greenish solid which precipitated was filtered off and washed with diisopropyl ether and petroleum ether. Drying under vacuum and over phosphoric anhydride at 40° C. yielded 26 g of crude 7-methyl-3-nitropyrazolo[1,5-a]pyrimidine (Yield=73%).

$^1$H NMR (DMSO-d$_6$; 200 MHz): 2.82 (s; 3H); 7.46 (d; J=4.5 Hz, 1H); 8.90 (d; J=4.5 Hz; 1H); 9.09 (s; 1H)

b) Preparation of 7-methylpyrazolo[1,5-a]pyrimidin-3-ylamine hydrochloride 19.3 g of 7-methyl-3-nitropyrazolo[1,5-a]-pyrimidine, 500 cc of methanol and 2.2 g of 5% palladium on charcoal with a water content of 50% were introduced into a 1 litre hydrogenation reactor. The medium was heated to about 60° C. and 7.7 bars of hydrogen were introduced. Following complete reduction, the reactor was cooled and the catalyst was filtered off. A stream of gaseous hydrochloric acid was passed through the filtrate, and the hydrochloride which precipitated was filtered off. Drying under vacuum and over phosphoric anhydride yielded 14.6 g of 7-methyl-pyrazolo[1,5-a]pyrimidin-3-ylamine hydrochloride (yield=72%).

$^1$H NMR (DMSO-d$_6$; 200 MHz): 2.75 (s; 3H); 7.17 (d; J=3.4 Hz, 1H); 8.40 (s; 1H); 8.75 (d; J=4.2 Hz; 1H); 10.77 (broad s; 3H)

EXAMPLE 4

Synthesis of 2,5,6,7-tetramethyl-pyrazolo[1,5-a]pyrimidin-3-ylamine hydrochloride

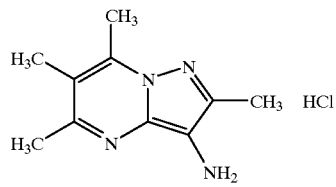

a) Preparation of 2,5,6,7-tetramethylpyrazolo-[1,5-a]pyrimidine 12.6 g of 3-methyl-2,4-pentanedione, 30 cc of acetic acid and 9.6 g of 3-amino-5-methylpyrazole were introduced into a 100 ml three-necked round-bottomed flask fitted with a magnetic stirrer, a condenser and a thermometer. The medium was refluxed for 1 hour. The acetic acid was evaporated off and the product was taken up in 50 cc of petroleum ether. The solid was filtered off and washed with petroleum ether. Drying under vacuum and over phosphoric anhydride yielded 15 g of 2,5,6,7-tetramethylpyrazolo[1,5-a]pyrimidine (yield=85.7%).

$^1$H NMR (DMSO-d$_6$; 200 MHz): 2.06 (s; 3H); 2.25 (s; 3H); 2.31 (s; 3H); 2.50 (s; 3H) 6.13 (s; 1H)

b) Preparation of 2,5,6,7-tetramethyl-3-nitropyrazolo[1,5-a]pyrimidine 50 cc of 98% sulphuric acid, in which 12.25 g of 2,5,6,7-tetramethylpyrazolo[1,5-a]pyrimidine obtained above in the preceding step had been dissolved, were introduced into a 100 ml three-necked round-bottomed flask fitted with a magnetic stirrer, a condenser, a dropping funnel and a thermometer. At about 0° C. 4.4 g of 100% nitric acid diluted in 2.5 cc of 98% sulphuric acid were added dropwise. At the end of the addition, stirring was continued at 0° C. for 1 hour and then the medium was poured onto 200 g of ice. The pH was brought to using 20% aqueous ammonia. The precipitate was filtered off. It was washed with water and with ethanol and with diisopropyl ether. Drying under vacuum and over phosphoric anhydride yielded 11 g of 2,5,6,7-tetramethyl-3-nitropyrazolo[1,5-a]pyrimidine (yield= 71.4%).

$^1$H NMR (DMSO-d$_6$; 200 MHz): 2.33 (s; 3H); 2.63 (s; 3H); 2.67 (s; 3H); 2.75 (s; 3 H)

c) Preparation of 2,5,6,7-tetramethylpyrazolo-[1,5-a]pyrimidin-3-ylamine hydrochloride 2.2 g of 2,5,6,7-tetramethyl-3-nitropyrazolo[1,5-a]pyrimidine, 40 cc of ethanol and 1 g of ammonium chloride were introduced into a 100 ml three-necked round-bottomed flask fitted with a magnetic stirrer, a condenser and a thermometer. The medium was brought to reflux, and 2.5 g of zinc powder were added in small portions in order to maintain the reflux. After 0.5 hour of refluxing, the zinciferous sludges were filtered. The filtrate was concentrated until it crystallized. The crystals were filtered off. Drying under vacuum and over phosphoric anhydride yielded 2 g of 2,5,6,7-tetramethylpyrazolo[1,5-a]pyrimidin-3-ylamine hydrochloride (yield=88.2%).

$^1$H NMR (DMSO-$d_6$; 200 MHz): 2.24 (s; 3H); 2.35 (s; 3H); 2.49 (s; 3H); 2.62 (s; 3H); 6.34 (broad s; 3H)

EXAMPLE 5

Synthesis of 5,7-di-tert-butylpyrazolo[1,5-a]pyrimidin-3-ylamine hydrochloride

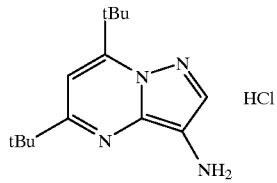

a) Preparation of 5,7-di-tert-butyl-3-nitropyrazolo[1,5-a]pyrimidine 36.85 g of 2,2,6,6-tetramethyl-3,5-heptanedione, 200 cc of acetic acid and 32.91 g of 4-nitro-2H-pyrazol-3-ylamine hydrochloride (prepared in accordance with H. Dorn and H. Dilcher, Liebigs Ann. Chem., 707,141, 1967) were introduced into a 500 ml three-necked flask fitted with a condenser, a thermometer and a magnetic bar. The mixture was refluxed for 8.5 hours. The solution was poured, hot, onto ice. The yellow solid which precipitated was filtered off. It was recrystallized from an acetic acid/water mixture. Drying under vacuum and over phosphoric anhydride yielded 25.4 g of 5,7-di-tert-butyl-3-nitropyrazolo[1,5-a]pyrimidine (yield=46%).

$^1$H NMR (DMSO-$d_6$; 200 MHz): 1.40 (s; 9H); 1.57 (s; 9H); 7.26 (s; 1H); 8.98 (s; 1H);

b) Preparation of 5,7-di-tert-butylpyrazolo[1,5-a]-pyrimidin-3-ylamine hydrochloride 8 g of 5,7-di-tert-butyl-3-nitropyrazolo-[1,5-a]pyrimidine, 350 cc of ethanol and 2 g of 5% palladium on charcoal with a water content of 50% were introduced into a 1 litre hydrogenation reactor. The medium was brought to 65° C., and 10.6 bars of hydrogen pressure were introduced. After 1.5 hours, the catalyst was filtered off, with the filtrate running into 5 M hydrochloric ethanol. This filtrate was treated with vegetable black. Filtration to remove the carbon black, evaporation of the ethanol, drying under vacuum and over phosphoric anhydride yielded 4.5 g of 5,7-di-tert-butylpyrazolo[1,5-a]pyrimidin-3-ylamine hydrochloride (yield=54.9%).

$^1$H NMR (DMSO-$d_6$; 200 MHz): 1.40 (s; 9H); 1.58 (s; 9H); 7.02 (s; 1H); 8.35 (s; 1H); 10.55 (broad s; 3H)

EXAMPLE 6

Synthesis of 5,7-di-trifluoromethyl-pyrazolo[1,5-a]pyrimidin-3-ylamine hydrochloride

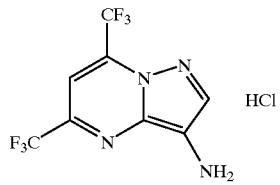

a) Preparation of 5,7-di-trifluoromethyl-3-nitropyrazolo[1,5-a]pyrimidine 31.2 g of 1,1,1,5,5,5-hexafluoro-2,4-pentanedione, 125 cc of acetic acid and 24.7 g of 4-nitro-2H-pyrazol-3-ylamine hydrochloride (prepared in accordance with H. Dorn and H. Dilcher, Liebigs Ann. Chem., 707, 141, 1967) were introduced into a 500 ml three-necked flask fitted with a condenser, a thermometer and a magnetic bar. The mixture was refluxed for 8.5 hours. The solution was poured, hot, onto ice. The yellow solid which precipitated was filtered off. It was washed with petroleum ether. Drying under vacuum and over phosphoric anhydride yielded 31.9 g of 5,7-di-trifluoromethyl-3-nitropyrazolo[1,5-a]pyrimidine (yield=71%).

$^1$H NMR (DMSO-$d_6$; 200MHz): 8.67 (s; 1H); 9.54 (s; 1H);

b) Preparation of 5,7-di-trifluoromethylpyrazolo-[1,5-a]pyrimidin-3-ylamine hydrochloride 3 g of 5,7-di-trifluoromethyl-3-nitro-pyrazolo[1,5-a]pyrimidine, 100 cc of ethanol and 0.4 g of 5% palladium on charcoal with a water content of 50% were introduced into a 250 cc hydrogenation reactor. 4.2 bars of hydrogen pressure were introduced. After 1 hour and 40 minutes, the catalyst was filtered off, with the filtrate running into 5 M hydrochloric ethanol. The ethanol was evaporated to yield 2 g of crude 5,7-di-trifluoromethylpyrazolo[1,5-a]pyrimidin-3-ylamine hydrochloride. 1.6 g of this crude product was recrystallized from 7 cc of hydrochloric ethanol. Drying under vacuum and over phosphoric anhydride yielded 1 g of 5,7-di-trifluoromethylpyrazolo[1,5-a]pyrimidin-3-ylamine hydrochloride (yield=32.6%).

$^1$H NMR (DMSO-$d_6$; 200 MHz): 8.23 (s; 1H); 8.72 (s; 1H); 9.54 (broad s; 3H)

Application Examples

EXAMPLES 1 to 4

Dyeing in an Alkaline Medium

The following dyeing compositions in accordance with the invention were prepared (contents in grams):

| COMPOSITION | 1 | 2 | 3 | 4 |
|---|---|---|---|---|
| Pyrazolo[1,5-a]pyrimidin-3-ylamine hydrochloride (oxidation base of formula (I)) | 0.51 | — | — | — |
| 2,5,6,7-Tetramethylpyrazolo-[1,5-a]pyrimidin-3-ylamine hydrochloride (oxidation base of formula (I)) | — | 0.68 | — | — |
| 5,7-Dimethylpyrazolo[1,5-a]-pyrimidin-3-ylamine hydrochloride (oxidation base of formula (I)) | — | — | 0.60 | — |

-continued

| COMPOSITION | 1 | 2 | 3 | 4 |
|---|---|---|---|---|
| 5,6,7-Trimethylpyrazolo[1,5-a]-pyrimidin-3-ylamine hydrochloride (oxidation base of formula (I)) | — | — | — | 0.64 |
| 2-Methyl-5-aminophenol (coupler) | 0.37 | 0.37 | 0.37 | 0.37 |
| Common dye vehicle No. 1 | (*) | (*) | (*) | (*) |
| Demineralized water q.s. | 100 g | 100 g | 100 g | 100 g |

| (*) Common dye vehicle No. 1: | |
|---|---|
| 96° Ethyl alcohol | 18 g |
| Sodium metabisulphite in 35% aqueous solution | 0.68 g |
| Pentasodium salt of diethylenetriamine-pentaacetic acid | 1.1 g |
| 20% Aqueous ammonia | 10.0 g |
| Demineralized water q.s. | 100 g |

Each of the above dyeing compositions was mixed at the time of use with an equal weight of a 20-volume (6% by weight) solution of hydrogen peroxide with a pH of 3.

The mixture obtained was applied to locks of natural grey hair containing 90% white hairs for 30 minutes. The locks were subsequently rinsed, washed with a standard shampoo, rinsed again and then dried.

The shades obtained are given in the following table:

| EXAMPLE | Resulting shade |
|---|---|
| 1 | Coppery orange |
| 2 | Coppery orange |
| 3 | Very light orange-yellow |
| 4 | Light orange-yellow |

EXAMPLES 5 to 7

Dyeing in an Alkaline Medium

The following dyeing compositions in accordance with the invention were prepared (contents in grams):

| COMPOSITION | 5 | 6 | 7 |
|---|---|---|---|
| 7-Methylpyrazolo[1,5-a]-pyrimidin-3-ylamine hydrochloride (oxidation base of formula (I)) | 0.55 | — | — |
| 5,7-Di-tert-butylpyrazolo[1,5-a]-pyrimidin-3-ylamine hydrochloride (oxidation base of formula (I)) | — | 0.85 | — |
| 2-Methoxy 5,7-dimethylpyrazolo[1,5-a]-pyrimidin-3-ylamine hydrochloride (oxidation base of formula (I)) | — | — | 0.69 |
| 2-Methyl-5-aminophenol (coupler) | 0.37 | 0.37 | 0.37 |
| Common dye vehicle No. 2 | () | () | (**) |
| Demineralized water q.s. | 100 g | 100 g | 100 g |

| (**) Common dye vehicle No. 2: | |
|---|---|
| 96° Ethyl alcohol | 20 g |
| Sodium metabisulphite | 0.23 g |
| Sequestrant | q.s. |
| 20% Aqueous ammonia | 10.0 g |
| Demineralized water q.s. | 100 g |

Each of the above dyeing compositions was mixed at the time of use with an equal weight of a 20-volume (6% by weight) solution of hydrogen peroxide with a pH of 3.

The mixture obtained was applied to locks of natural grey hair containing 90% white hairs for 30 minutes. The locks were subsequently rinsed, washed with a standard shampoo, rinsed again and then dried.

The shades obtained are given in the following table:

| EXAMPLE | Resulting shade |
|---|---|
| 5 | Coppery |
| 6 | Yellow |
| 7 | Coppery gold |

EXAMPLES 8

Dyeing in an Alkaline Medium

The following dyeing composition was prepared:

| | |
|---|---|
| 5,7-Di-trifluoromethylpyrazolo[1,5-a]-pyrimidin-3-ylamine hydrochloride (oxidation base of formula (I)) | 0.92 g |
| 2-Methyl-5-aminophenol (coupler) | 0.37 g |
| Benzyl alcohol | 2 g |
| Polyethylene glycol containing 6 mol of ethylene oxide | 3 g |
| 96° Ethanol | 18 g |
| $C_8$–$C_{10}$-Alkyl polyglucoside in aqueous solution containing 60% of active substance, buffered with ammonium citrate, sold under the name ORAMIX CG110 ® by the company SEPPIC | 6 g |
| Aqueous ammonia containing 20% $NH_3$ | 10 g |
| Sodium metabisulphite | 0.23 g |
| Sequestrant | q.s. |
| Demineralized water q.s. | 100 g |

The above composition was mixed at the time of use with an equal weight of a 20-volume (6% by weight) solution of hydrogen peroxide with a pH of 3.

The mixture obtained was applied to locks of natural grey hair containing 90% white hairs for 30 minutes. The locks were subsequently rinsed, washed with a standard shampoo, rinsed again and then dried.

The locks of hair had been dyed in a reddish copper shade.

What is claimed is:

1. A composition for the oxidation dyeing of keratinous fibers wherein said composition comprises, in a medium suitable for dyeing keratinous fibers, at least one coupler chosen from meta-phenylenediamines, meta-aminophenols, meta-diphenols and heterocyclic couplers, and at least one 3-aminopyrazolo(1,5-a)pyrimidine chosen from compounds of formula (I) and acid and base addition salts thereof:

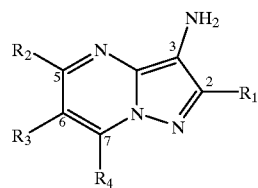

(I)

in which
R$_1$, R$_2$, R$_3$ and R$_4$ are identical or different and are chosen from a hydrogen atom, a halogen atom, a C$_1$–C$_4$ alkyl radical, a C$_1$–C$_4$ trifluoroalkyl radical, a C$_1$–C$_4$ alkoxy radical, an aryl radical, a C$_1$–C$_4$ monohydroxyalkyl radical, a C$_2$–C$_4$ polyhydroxyalkyl radical, a C$_1$–C$_4$ (C$_1$–C$_4$ alkoxy)alkyl radical, a C$_1$–C$_4$ aminoalkyl radical, a C$_1$–C$_4$ (C$_1$–C$_4$ alkyl)aminoalkyl radical, a C$_1$–C$_4$ di(C$_1$–C$_4$ alkyl)aminoalkyl radical, a C$_1$–C$_4$ monohydroxy (C$_1$–C$_4$ alkyl)aminoalkyl radical and a C$_1$–C$_4$ di(hydroxy(C$_1$–C$_4$ alkyl))aminoalkyl radical,
wherein said at least one coupler and said at least one 3-aminopyrazolo(1,5-a)pyrimidine are present in said composition in a combined amount effective to dye keratinous fibers.

2. The composition of claim 1 wherein said keratinous fibers are human keratinous fibers.

3. The composition of claim 2 wherein said human keratinous fibers are hair.

4. The composition of claim 1, wherein said at least one 3-aminopyrazolo(1,5-a)-pyrimidine is chosen from:
pyrazolo(1,5-a) pyrimidin-3-ylamine;
5,7-dimethylpyrazolo(1,5-a)pyrimidin-3-ylamine;
5,6,7-trimethylpyrazolo(1,5-a)pyrimidin-3-ylamine;
7-methylpyrazolo(1,5-a)pyrimidin-3-ylamine;
5-methylpyrazolo(1,5-a)pyrimidin-3-ylamine;
7-methoxypyrazolo(1,5-a)pyrimidin-3-ylamine;
5-methoxypyrazolo(1,5-a) pyrimidin-3-ylamine;
7-methoxy-5-methylpyrazolo(1,5-a) pyrimidin-3-ylamine;
2,5,6,7-tetramethylpyrazolo(1,5-a)pyrimidin-3-ylamine;
2-methoxy-5,7-dimethylpyrazolo(1,5-a)pyrimidin-3-ylamine;
5,7-di-tert-butylpyrazolo(1,5-a)pyrimidin-3-ylamine;
5,7-di-trifluoromethylpyrazolo(1,5-a)pyrimidin-3-ylamine;
2,6-dimethylpyrazolo(1,5-a)pyrimidin-3-ylamine;
2-chloro-5,7-dimethylpyrazolo(1,5-a)pyrimidin-3-ylamine;
7-methyl 2-tert-butyl-5-trifluoromethyl-pyrazolo(1,5-a) pyrimidin-3-ylamine; and the acid and base addition salts thereof.

5. The composition of claim 1, wherein said at least one 3-aminopyrazolo(1,5-a)-pyrimidine is chosen from:
pyrazolo(1,5-a)pyrimidin-3-ylamine;
5,7-dimethylpyrazolo(1,5-a)pyrimidin-3-ylamine;
5,6,7-trimethylpyrazolo(1,5-a)pyrimidin-3-ylamine;
2,5,6,7-tetramethylpyrazolo(1,5-a)pyrimidin-3-ylamine;
2-methoxy-5,7-dimethylpyrazolo(1,5-a) pyrimidin-3-ylamine;
5,7-di-trifluoromethylpyrazolo(1,5-a)pyrimidin-3-ylamine;
7-methylpyrazolo(1,5-a)pyrimidin-3-ylamine;
5-methylpyrazolo(1,5-a)pyrimidin-3-ylamine;
and acid and base addition salts thereof.

6. The composition of claim 1, wherein said at least one, 3-aminopyrazolo(1,5-a)-pyrimidine represents from 0.0005 to 12% by weight relative to the total weight of the dyeing composition.

7. The composition of claim 6, wherein said at least one 3-aminopyrazolo(1,5-a)-pyrimidine represents from 0.005 to 6% by weight relative to the total weight of the dyeing composition.

8. The composition of claim 1, wherein said medium suitable for dyeing comprises water, a water/alcohol mixture or a mixture of water and at least one organic solvent, wherein said at least one organic solvent is chosen from C$_1$–C$_4$ lower alkanols, glycerol, glycols and glycol ethers, aromatic alcohols, and mixtures thereof.

9. The composition of claim 8, wherein said at least one organic solvent is present in proportion ranging from 1 to 40% by weight approximately relative to the total weight of the dye composition.

10. The composition of claim 9, wherein said at least one organic solvent is present in proportions ranging from 5 to 30%.

11. The composition of claim 1, where said composition has a pH ranging from 3 to 12.

12. The composition of claim 11, wherein said composition has a pH ranging from 5 to 11.

13. The composition of claim 1, wherein said at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethoxy)benzene, 2-amino-4-(β-hydroxyethylamino)-1-methoxybenzene, 1,3-diaminobenzene, 1,3-bis(2,4-diaminophenoxy)propane, sesamol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and the addition salts thereof.

14. The composition of claim 1, wherein said at least one coupler represents from 0.0001 to 10% by weight relative to the total weight of the dyeing composition.

15. The composition of claim 14, where said at least one coupler represents from 0.005 to 5% by weight relative to the total weight of the dyeing composition.

16. The composition of claim 1, wherein said composition additionally contains at least one oxidation base other than said compounds of formula I.

17. The composition of claim 16, wherein said additional oxidation base is chosen from para-phenylenediamines, bisphenylalkylenediamines, para-aminophenols, ortho-aminophenols and heterocyclic bases which are different from the 3-aminopyrazolo(1,5-a)pyrimidines of formula (I).

18. The composition of claim 17, wherein said para-phenylenediamines are chosen from para-phenylenediamine, para-tolylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis((β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and the acid addition salts thereof.

19. The composition of claim 18, wherein said para-phenyldiamines are chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-diethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

20. The composition of claim 17, wherein said bisphenylalkylenediamines are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)-ethylenediamine, 1,8-bis(2,5-diaminophenoxy)-3,5-dioxaoctane, and the acid addition salts thereof.

21. The composition of claim 17, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

22. The composition claim 17, wherein said ortho-aminophenols are chosen from 2-aminophenol, 2-amino-5-methylphenol, 2-amino-6-methylphenol, 5-acetamido-2-aminophenol, and the acid addition salts thereof.

23. The composition of claim 17, where said other heterocyclic bases are chosen from pyridine derivatives, pyrimidine derivatives and pyrazole derivatives.

24. The composition of claim 20, wherein said at least one additional oxidation base represents from 0.0005 to 12% by weight of the total weight of the dyeing composition.

25. The composition of claim 24, wherein said at least one additional oxidation base represents from 0.005 to 6% by weight of the total weight of the dyeing composition.

26. The composition of claim 1, wherein said acid addition salts are chosen from hydrochlorides, hydrobromides, sulphates, citrates, succinates, tartrates, lactates and acetates.

27. The composition of claim 1, wherein said base addition salts are chosen from sodium hydroxide solution, potassium hydroxide solution, aqueous ammonia, and amines.

28. The composition of claim 1, wherein said composition additionally contains at least one direct dye.

29. The composition of claim 28, wherein said at least one direct dye is chosen from nitro derivatives of benzene.

30. The composition of claim 1, wherein said composition additionally contains at least one adjuvant chosen from anionic, cationic, nonionic, amphoteric and zwitterionic surfactants, anionic, cationic, nonionic, amphoteric and zwitterionic polymers, organic and inorganic thickeners, antioxidants, penetration agents, sequestrants, fragrances, buffers, dispersants, conditioners, film forming agents, ceramides, preserving agents and opacifiers.

31. The composition of claim 30, wherein said conditioners are chosen from modified and unmodified, volatile and nonvolatile silicones.

32. A method for dyeing keratinous fibers, comprising the steps of contacting said fibers for a time sufficient to achieve color development, with a dye composition of claim 1.

33. The method of claim 32, wherein said keratinous fibers are human keratin fibers.

34. The method of claim 33, wherein said human keratinous fibers are hair.

35. The method of claim 32, wherein said dye composition is mixed at the time of application with an oxidizing composition comprising, in a medium suitable for dyeing, at least one oxidizing agent present in an amount sufficient for color development.

36. The method of claim 32, wherein said dye composition additionally contains at least one oxidation catalyst.

37. The method of claim 35, wherein said at least one oxidizing agent is chosen from hydrogen peroxide, urea peroxide, alkali metal bromates, persalts, and enzymes.

38. The method of claim 37, wherein said persalts are chosen from perborates and persulphates.

39. The method of claim 37, wherein said enzymes are chosen from peroxidases and oxidoreductases with 2 unpaired electrons.

40. The method of claim 35, wherein said oxidizing composition is added simultaneously, sequentially, or separately at the time the dye composition is applied.

41. The method of claim 32, wherein said time ranges from 3 to 50 minutes.

42. The method of claim 41, wherein said time ranges from 5 to 30 minutes.

43. The method of claim 35, wherein said oxidizing composition has a pH ranging from 3 to 12.

44. The method of claim 43, wherein said oxidizing composition has a pH ranging from 5 to 11.

45. The method of claim 35, wherein said oxidizing composition additionally contains at least one adjuvant chosen from anionic, cationic, nonionic, amphoteric and zwitterionic surfactants, anionic, cationic, nonionic, amphoteric and zwitterionic polymers, organic and inorganic thickeners, antioxidants, penetration agents, sequestrants, fragrances, buffers, dispersants, conditioners, film forming agents, ceramides, preserving agents and opacifiers.

46. The method of claim 32, wherein said color development occurs at an acidic, neutral or alkaline pH.

47. The composition of claim 1, wherein said composition further comprises an oxidizing composition comprising, in a medium suitable for dyeing, at least one oxidizing agent present in an amount sufficient for color development of said composition on keratinous fibers.

48. The composition of claim 47, wherein said oxidizing agent is chosen from hydrogen peroxide, urea peroxide, alkali metal bromates, persalts, and enzymes.

49. The composition of claim 48, wherein said persalts are chosen from perborates and persulphates.

50. The composition of claim 48, wherein said enzymes are chosen from peroxidases and oxidoreductases with 2 unpaired electrons.

51. The composition of claim 47, wherein said oxidizing composition has a pH ranging from 3 to 12.

52. The composition of claim 51, wherein said oxidizing composition has a pH ranging from 5 to 11.

53. The composition of claim 47, wherein said oxidizing composition additionally contains at least one adjuvant chosen from anionic, cationic, nonionic, amphoteric and zwitterionic surfactants, anionic, cationic, nonionic, amphoteric and zwitterionic polymers, organic and inorganic thickeners, antioxidants, penetration agents, sequestrants, fragrances, buffers, dispersants, conditioners, film forming agents, ceramides, preserving agents and opacifiers.

54. The composition of claim 1, wherein said composition contains at least one oxidation catalyst.

55. The composition of claim 1, said composition being in the form of a liquid, a cream, a gel or any other form suitable for dyeing keratinous fibers.

56. A multi-compartment dyeing device or kit for dyeing keratin fibers, comprising at least two compartments, wherein a first compartment contains a dyeing composition according to claim 1 and a second compartment contains an oxidizing composition.

* * * * *

UNITED STATES PATENT AND TRADEMARK OFFICE
CERTIFICATE OF CORRECTION

PATENT NO.   : 6,248,137 B1
DATED        : June 19, 2001
INVENTOR(S)  : Eric Terranova et al.

It is certified that error appears in the above-identified patent and that said Letters Patent is hereby corrected as shown below:

Column 17, claim 19,
Line 16, "2,6-diethyl" should read -- 2,6-dimethyl --.

Signed and Sealed this

Twenty-fifth Day of December, 2001

Attest:

*Attesting Officer*

JAMES E. ROGAN
*Director of the United States Patent and Trademark Office*